United States Patent
Lai et al.

(10) Patent No.: US 8,410,530 B2
(45) Date of Patent: Apr. 2, 2013

(54) SENSITIVE FIELD EFFECT TRANSISTOR APPARATUS

(75) Inventors: Chao-Sung Lai, Tao-Yuan (TW);
Cheng-En Lue, Songshan District (TW);
Chia-Ming Yang, Ziguan Township, Kaohsiung County (TW); Szu-Chieh Wang, Xindian (TW)

(73) Assignee: Chang Gung University (TW)

( * ) Notice: Subject to any disclaimer, the term of this patent is extended or adjusted under 35 U.S.C. 154(b) by 727 days.

(21) Appl. No.: 12/591,466

(22) Filed: Nov. 20, 2009

(65) Prior Publication Data
US 2010/0301399 A1 Dec. 2, 2010

(30) Foreign Application Priority Data
May 26, 2009 (TW) .............................. 98117383 A

(51) Int. Cl.
*H01L 29/78* (2006.01)

(52) U.S. Cl. ....................................................... 257/253

(58) Field of Classification Search .................. 257/213, 257/253, E29.001, E29.242
See application file for complete search history.

(56) References Cited

U.S. PATENT DOCUMENTS
8,283,704 B2 * 10/2012 Tsukada ........................ 257/253

FOREIGN PATENT DOCUMENTS
DE 3236757 A1 * 4/1984

OTHER PUBLICATIONS

Lai et al, Chao-Sung, Novel Research of Differential PH Response Based on SI3N4 EIS With Different Substrates and Structures, 2008 International Electron Devices and Materials Symposia, Nov. 28-29, 2008, National Chung Hsing University, Taichung, Taiwan, R.O.C.
Wang et al, Szu-Chieh, Single Si3N4 Layer on Dual Substrate for pH Sensing Micro Sensor, 2008 International Electron Devices and Materials Symposia, Nov. 28-29, 2008, National Chung Hsing University, Taichung, Taiwan, R.O.C.

* cited by examiner

*Primary Examiner* — Hsien Ming Lee
*Assistant Examiner* — Michele Fan
(74) *Attorney, Agent, or Firm* — Bacon & Thomas, PLLC

(57) ABSTRACT

The invention discloses a sensitive field effect transistor apparatus, which uses an inorganic membrane to sense hydrogen ions. The invention adopts the membrane with high deformation stress. The sensitivity of the sensitive membrane to hydrogen ions is adjusted through altering the membrane thickness and changing the substrate type and doped concentration. A differential amplifier is used to read a signal to form the inorganic Ion Sensitive Field Effect Transistor/Reference Field Effect Transistor apparatus.

2 Claims, 3 Drawing Sheets

SENSITIVE FIELD EFFECT TRANSISTOR APPARATUS

BACKGROUND OF THE INVENTION

1. Field of the Invention

The invention relates to a Sensitive Field Effect Transistor apparatus, particularly to an Ion Sensitive Field Effect Transistor/Reference Field Effect Transistor/quasi Reference Electrode apparatus.

2. Description of the Prior Art

The initial concept of Ion Sensitive Field Effect Transistor (ISFET) was proposed by P. Bergveld in 1970 first. It has been improved and developed continuously. Since the development of Ion Sensitive Field Effect Transistor, the specific sensitive membrane material had been developed for many pH Ion Sensitive Field Effect Transistors (pH-ISFET). This material has high sensitivity and will not be interfered by non-ideal effect. In addition, due to the structure of Ion Sensitive Field Effect Transistor is similar to the structure of Metal-Oxide-Semiconductor Field Effect Transistor, the Complementary Metal Oxide Semiconductor (CMOS) process can be used to manufacture the Ion Sensitive Field Effect Transistor and to be microminiaturized. The Ion Sensitive Field Effect Transistor has very high biocompatibility, thus it is widely applied to the fields, such as biochip, human body inspection etc.

However, there still is a big problem to be solved in the manufacturing of micro Ion Sensitive Field Effect Transistor system. This problem relates to the reference electrode. At present, all Ion Sensitive Field Effect Transistor systems must use the conventional glass reference electrode (such as Ag/AgCl or calomel electrode) to provide the stable potential. However, the electrode stability and service life of these reference electrodes will be reduced due to the decrease of internal ion exchange solution under the microminiaturization process. Thus, it is very difficult to microminiaturize the reference electrode. It has seriously restrained the application and development of Ion Sensitive Field Effect Transistor on the biomedical field and human body inspection and diagnosis.

Matsuo proposed the Reference Field Effect Transistor (REFET) apparatus first in 1978. At present, the research of this element can be divided into three categories mainly:

1. Add an ion-blocking layer on the original inorganic membrane, in order to reduce the number of ionic bonding on the surface of sensitive membrane.
2. Employ the polymer to form an ion-blocking membrane. However, it is limited to the problem of membrane thickness. The membrane thickness must be increased, in order to improve the defect of membrane pore. When the membrane thickness is increased, the transconductance of element will be decayed, which will lead to the mismatch of system operation. In addition, this kind of membrane has the stability and high sensitivity problems.
3. Employ the polymer to form an ion-unblocking membrane. It can solve the above-mentioned decay problem of transconductance. It is also the most mature and stable membrane with low sensitivity at present. Even so, the service life of this kind of membrane is still short.

The development of organic Reference Field Effect Transistor (using PVC membrane) is mature, where the sensitivity can be reduced to about 1 mV/pH to 2 mV/pH at present. However, there organic membrane and the semiconductor element still are the problems of complicated process and incompatible structure. Thus, the development of inorganic Reference Field Effect Transistor not only can simplify the process, but also can be compatible with the CMOS process completely and can avoid the transconductance decay of organic membrane. It will be an innovative development on the fields of Reference Field Effect Transistor and Ion Sensitive Field Effect Transistor.

The structure of Reference Field Effect Transistor and Ion Sensitive Field Effect Transistor are very similar. The main difference is that the Ion Sensitive Field Effect Transistor is very sensitive to the target ion (such as hydrogen ion, sodium ion, and potassium ion), but the Reference Field Effect Transistor is less sensitive to the target ion. The Ion Sensitive Field Effect Transistor/Reference Field Effect Transistor should have the quasi Reference Electrode (qRE) to provide the bias voltage to the sensing system to form the circuit. The differential amplifier is used to differentiate the output voltage of quasi Reference Electrode. The final obtained output voltage is the output ion concentration of Ion Sensitive Field Effect Transistor/Reference Field Effect Transistor system. The influence of voltage between unstable solid and liquid interface can be offset by the differential amplifier. From the above-mentioned description, the Reference Field Effect Transistor with low ion sensitivity can be formed as the combination of Ion Sensitive Field Effect Transistor/Reference Field Effect Transistor/quasi Reference Electrode (IS FET/REFET/qRE).

In the conventional Ion Sensitive Field Effect Transistor, due to the part of reference electrode is difficult to be microminiaturized and integrated into the integrated circuit (IC), thus the Ion Sensitive Field Effect Transistor/Reference Field Effect Transistor system has been proposed. When the ion sensitivity is reduced, it is necessary to be dependent on a layer of extra organic membrane. Thus, the complexity of process is increased, and the service life is also reduced.

From the above-mentioned reason, it is known that the development of Reference Field Effect Transistor is paid more attention day by day. In order to respond the future demand, it is necessary to develop relevant technology of inorganic Reference Field Effect Transistor apparatus, in order to reduce the cost of operation manpower and manufacturing time, and reach the purpose of energy conservation and carbon reduction effectively.

SUMMARY OF THE INVENTION

The invention employs the semiconductor process technology to form the Sensitive Field Effect Transistor, namely the Ion Sensitive Field Effect Transistor/Reference Field Effect Transistor apparatus. The invention employs a semiconductor substrate, and the well is formed in the substrate to form the inorganic Ion Sensitive Field Effect Transistor/Reference Field Effect Transistor.

The inorganic Ion Sensitive Field Effect Transistor of the invention comprises a semiconductor substrate of P-type silicon chip, wherein the N-well is formed in P-type silicon chip; the electrode formed by the source, drain, and N-type ion is formed in the N-well; the metal wire is connected to the surface of electrode; the silicon dioxide is formed on the surface of P-type silicon chip between the electrode and metal wire; the single-layer silicon nitride is formed on the surface of N-well, because the silicon nitride will not influence the sensitivity of hydrogen ion, it can be used for the inorganic Ion Sensitive Field Effect Transistor; the photo resistance layer is formed on the surface of silicon dioxide and the surface of metal wire to form the inorganic Ion Sensitive Field Effect Transistor.

The Reference Field Effect Transistor of the invention comprises a semiconductor substrate of P-type silicon chip, wherein the P-well is formed in P-type silicon chip; the electrode formed by the source, drain, and P-type ion is formed in the P-well; the metal wire is connected to the surface of electrode; the silicon dioxide is formed on the surface of P-type silicon chip between the second electrode and metal wire; the single-layer silicon nitride is formed on the surface of P-well, it can reduce the sensitivity of hydrogen ion effectively, so that the surface will not be sensitive to hydrogen ion; the photo resistance layer is formed on the surface of silicon dioxide and the surface of metal wire to form the Reference Field Effect Transistor.

In the invention, the silicon dioxide is formed on the surface of P-type silicon chip between the inorganic Ion Sensitive Field Effect Transistor and Reference Field Effect Transistor. The metal wire is formed at both sides of silicon dioxide. The platinum is formed on the surface of silicon dioxide. The photo resistance layer is formed on the surface of silicon dioxide and the surface of metal wire around both sides of platinum, so as to form the inorganic Ion Sensitive Field Effect Transistor/Reference Field Effect Transistor apparatus of the invention.

The invention integrates the Ion Sensitive Field Effect Transistor and Reference Field Effect Transistor in the same wafer. It is different from the prior art, which forms two independent elements. Thus the utilization is more convenient.

The invention uses the inorganic membrane to sense low hydrogen ion. It adopts the membrane with high deformation stress. The sensitivity of sensitive membrane on hydrogen ion can be adjusted through altering the membrane thickness and changing the substrate type and doped concentration.

The invention can solve the problems of stability and service life of reference electrode encountered in the microminiaturization process. The differential amplifier can also be used to reduce the non-ideal effect of element.

Therefore, the advantage and spirit of the invention can be understood further by the following detail description of invention and attached Figures.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

The invention selects the semiconductor process technology and uses the N-type or P-type semiconductor substrate, or the well to form the inorganic Ion Sensitive Field Effect Transistor/Reference Field Effect Transistor apparatus.

Figure 1:
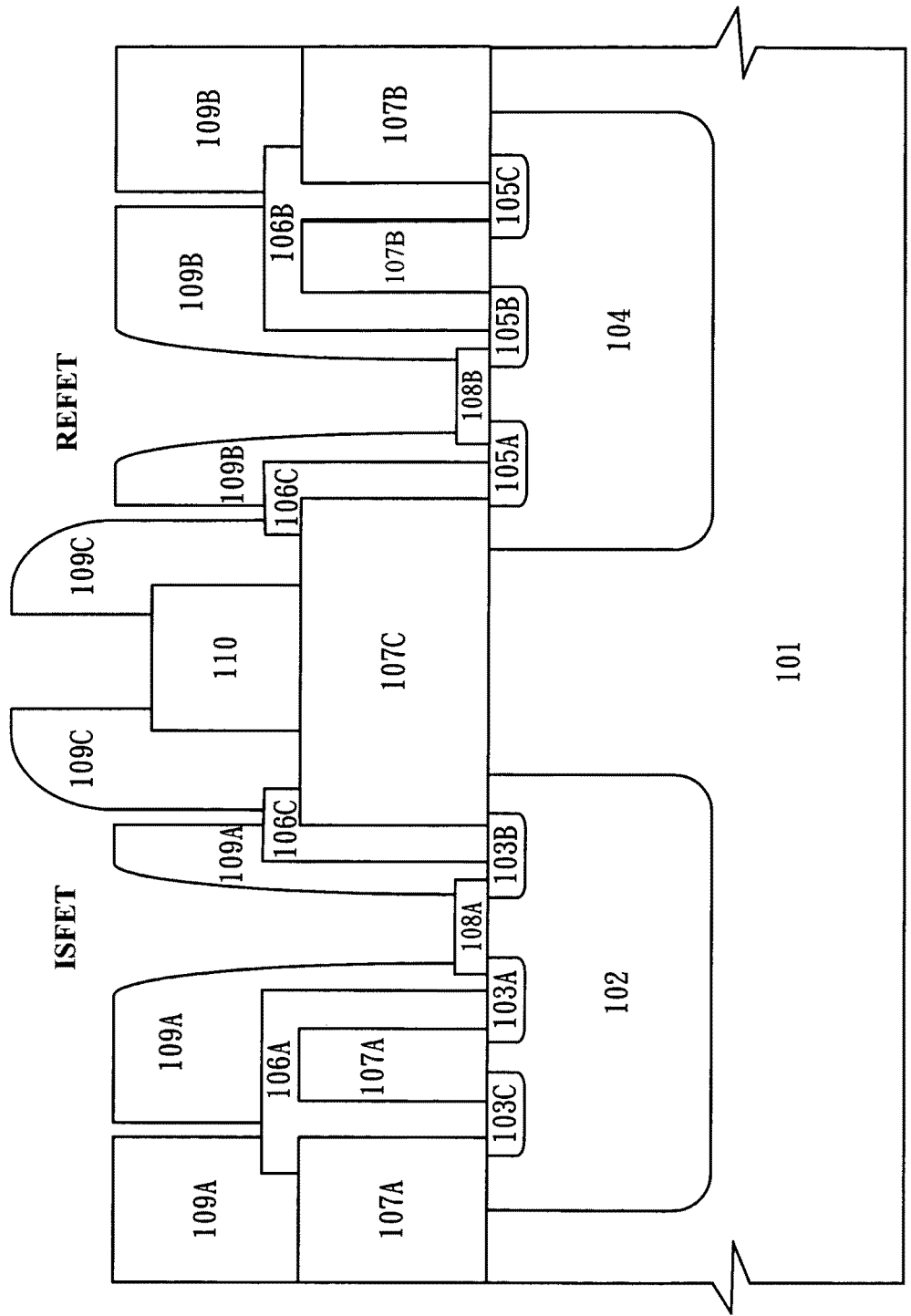
FIG. 1 schematically shows a preferred embodiment of the invention.

As shown in FIG. 1, a preferred embodiment of inorganic Ion Sensitive Field Effect Transistor/Reference Field Effect Transistor is illustrated, wherein the inorganic Ion Sensitive Field Effect Transistor (ISFET) is shown on the left hand side and the Reference Field Effect Transistor (REFET) is shown on the right hand side.

As shown in FIG. 1 again, the inorganic Ion Sensitive Field Effect Transistor on the left hand side comprises a semiconductor substrate of P-type silicon chip 101, the N-well 102 is formed in P-type silicon chip 101; the first electrode 103 formed in the N-well 102 is fabricated by the first source 103A, the first drain 103B, and N-type ion (N+) 103C. The first metal wire 106A is connected to the surface of the first electrode 103; the first silicon dioxide ($SiO_2$) 107A is formed on the surface of P-type silicon chip 101 between the first electrode 103 and the first metal wire 106A; the first single-layer silicon nitride ($Si_3N_4$) 108A is formed on the surface of N-well 102 to form the first hydrogen ion sensitive membrane, due to the first silicon nitride 108A will not influence the sensitivity of hydrogen ion, it can be used for the inorganic Ion Sensitive Field Effect Transistor; the first photo resistance layer 109A is formed on the surface of the first silicon dioxide 107A and the surface of the first metal wire 106A to form the inorganic Ion Sensitive Field Effect Transistor.

Still as shown in FIG. 1 again, the Reference Field Effect Transistor on the right hand side comprises a semiconductor substrate of P-type silicon chip 101, wherein the P-well 104 is formed in P-type silicon chip 101; the second electrode 105 formed by the second source 105A, the second drain 105B, and the second P-type ion (P+) 105C is formed in the P-well 104; the second metal wire 106 is connected to the surface of the second electrode 105; the second silicon dioxide 107B is formed on the surface of P-type silicon chip 101 between the second electrode 105 and the second metal wire 106B; the second single-layer silicon nitride 108B is formed on the surface of P-well 104 to form the second hydrogen ion sensitive membrane, it can reduce the sensitivity of hydrogen ion effectively, so that the surface will not be sensitive to hydrogen ion; the second photo resistance layer 109B is formed on the surface of the second silicon dioxide 107B and the surface of the second metal wire 106B to form the Reference Field Effect Transistor. Excepting the silicon nitride ($Si_3N_4$), the tantalum oxide ($Ta_2O_5$) and aluminum oxide ($Al_2O_3$) can be used to make the hydrogen ion sensing membrane as well.

As shown in FIG. 1, between the inorganic Ion Sensitive Field Effect Transistor at the left hand side and the Reference Field Effect Transistor at the right hand side, the third silicon dioxide 107C is formed on the surface of P-type silicon chip 101; the third metal wire 106C is formed at both sides of the third silicon dioxide 107C; the quasi platinum (Pt) Reference Electrode 110 is formed on the surface of the third silicon dioxide 107C; the third photo resistance layer 109B is formed on the surface of the third silicon dioxide 107C and the surface of the third metal wire 106C around both sides of platinum 110, so as to form the inorganic Ion Sensitive Field Effect Transistor/Reference Field Effect Transistor apparatus of the invention, wherein the quasi Reference Electrode is usually made up of gold or platinum.

Figure 2:
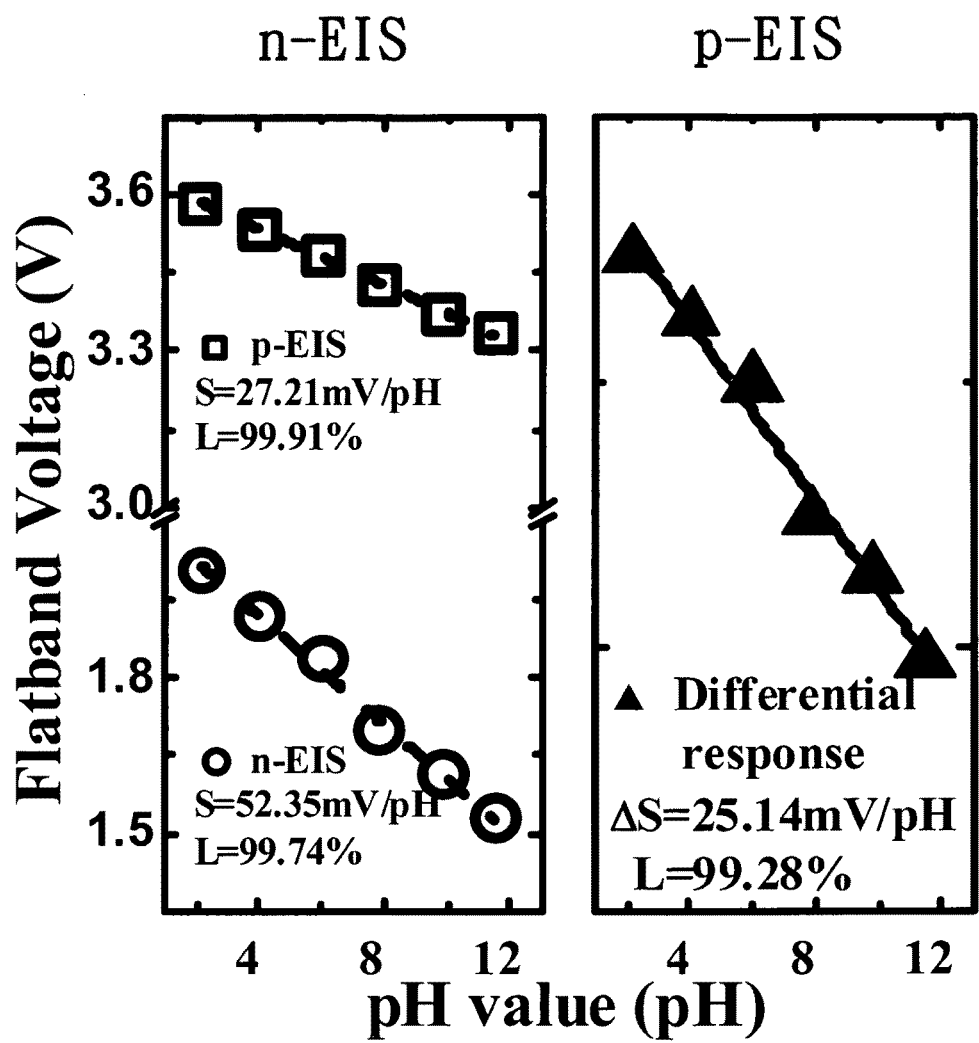
FIG. 2 schematically shows the sensitivity of hydrogen ion and the output voltage of differential response.

FIG. 2 shows the sensitivity of hydrogen ion and the output voltage of differential response. The sensitivity and differential response are measured for the P-type Electrolyte Insulator Semiconductor (p-EIS) and (N-type Electrolyte Insulator Semiconductor (n-EIS). The results show that the P-type Electrolyte Insulator Semiconductor owns lower sensitivity on hydrogen ion, which is about 27.2 mV/pH only. The N-type Electrolyte Insulator Semiconductor owns higher slope, and the sensitivity is about 52.4 mV/pH. They are subtracted to obtain a differential response, and the sensitivity is about 25.14 mV/pH. This sensitivity will be applied to the output voltage and sensitivity fields used in the ISFET/REFET/qRE.

Figure 3:
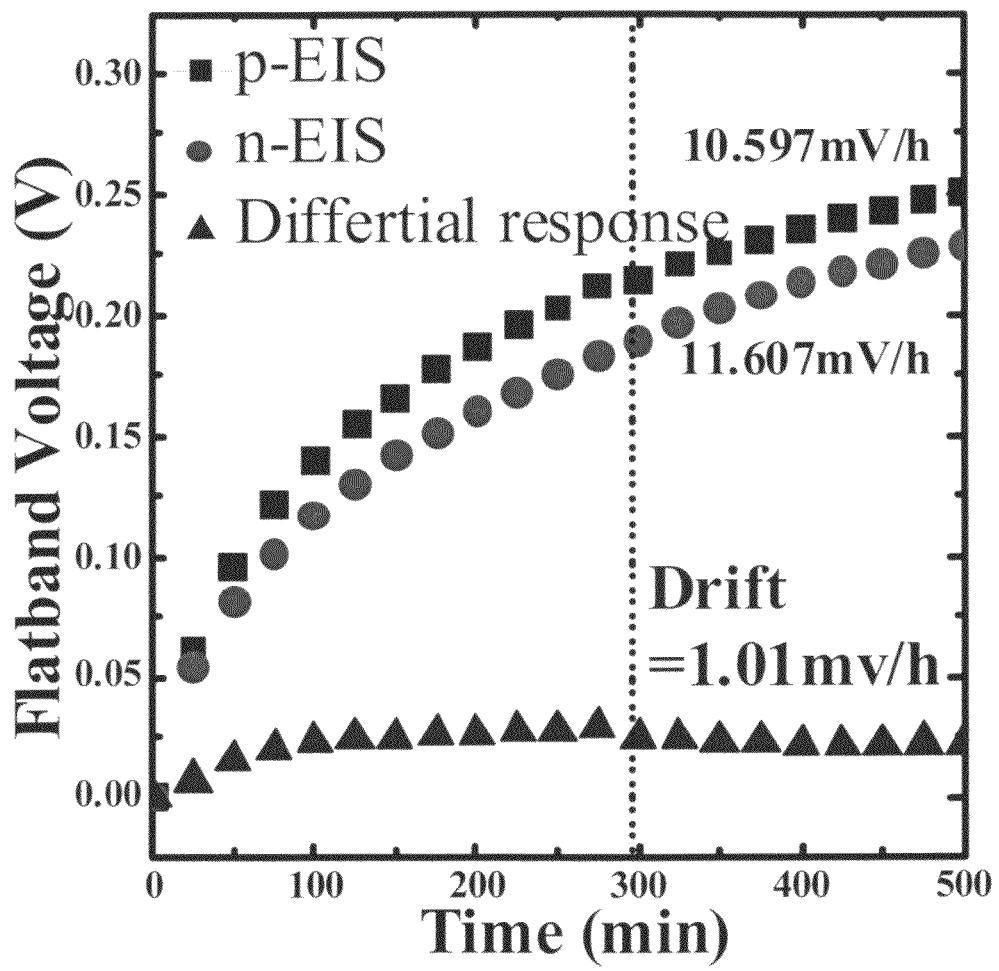
FIG. 3 schematically shows the result for drift effect of the invention.

In addition, FIG. 3 shows the result of drift effect. The long-term stability is also a requirement of sensitive element. The drift of the above-mentioned element can be reduced to 1 mV/h effectively. Thus the non-ideal effect can be improved effectively, and the accuracy of element can be increased greatly.

The invention integrates the Ion Sensitive Field Effect Transistor and Reference Field Effect Transistor in the same wafer. It is different from the known art, which forms two independent elements. Thus the utilization is more convenient. The invention uses the inorganic membrane to sense low hydrogen ion. It adopts the membrane with high deformation stress. The sensitivity of sensitive membrane on hydrogen ion can be adjusted through altering the membrane thickness or changing the substrate type and doped concentration. The invention can solve the problems of stability and service life of reference electrode encountered in the micro-miniaturization process. The differential amplifier can also be used to reduce the non-ideal effect of element.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A sensitive field effect transistor apparatus comprises:
an inorganic ion sensitive field effect transistor; and
an inorganic reference field effect transistor connected to the inorganic ion sensitive field effect transistor to form the sensitive field effect transistor apparatus, wherein the inorganic reference field effect transistor, comprises :
a semiconductor substrate of a p-type silicon chip, a p-well formed in the p-type silicon chip:
a second electrode being formed in the p-well, the second electrode including a second source, a second drain and a second p-type ion;
a second metal wire being connected to a surface of the second electrode;
a second silicon dioxide being formed on a surface of the p-type silicon chip between the second electrode and the second metal wire;
a second hydrogen ion sensitive membrane being formed on a surface of the p-well, wherein the second hydrogen ion sensitive membrane comprises silicon nitride; and
a second photo resistance layer being formed on a surface of the second silicon dioxide and a surface of the second metal wire.

2. A sensitive field effect transistor comprises:
an inorganic ion sensitive field effect transistor comprising:
a semiconductor substrate of a p-type silicon chip, a n-well formed in the p-type silicon chip;
a first electrode being formed in the n-well, the first electrode including a first source, a first drain and a first n-type ion;
a first metal wire being connected to a surface of the first electrode;
a first silicon dioxide being formed on a surface of the p-type silicon chip between the first electrode and the first metal wire;
a first hydrogen ion sensitive membrane being formed on a surface of the n-well, wherein the first hydrogen ion sensitive membrane is selected from the group consisting of silicon nitride, tantalum oxide, and aluminum oxide; and
a first photo resistance layer being formed on a surface of the first silicon dioxide and a surface of the first metal wire;
an inorganic reference field effect transistor comprising:
the semiconductor substrate of the p-type silicon chip, a p-well formed in the p-type silicon chip;
a second electrode being formed in the p-well, the second electrode including a second source, a second drain and a second p-type ion;
a second metal wire being connected to a surface of the second electrode;
a second silicon dioxide being formed on a surface of the p-type silicon chip between the second electrode and the second metal wire;
a second hydrogen ion sensitive membrane being formed on a surface of the p-well, wherein the second hydrogen ion sensitive membrane is selected from the group consisting of silicon nitride, tantalum oxide, and aluminum oxide; and
a second photo resistance layer being formed on a surface of the second silicon dioxide and a surface of the second metal wire;
a third silicon dioxide being formed on a surface of the p-type silicon chip;
a third metal wire being formed at both sides of the third silicon dioxide;
a quasi reference electrode being formed on a surface of the third silicon dioxide, wherein the quasi reference electrode is selected from the group consisting of a gold and a platinum; and
a third photo resistance layer being formed on the surface of the third silicon dioxide and a surface of the third metal wire around both sides of the quasi reference electrode.

* * * * *